United States Patent
Morf et al.

(10) Patent No.: US 11,478,663 B2
(45) Date of Patent: Oct. 25, 2022

(54) IMAGERS IN RADIATION THERAPY ENVIRONMENT

(71) Applicant: Varian Medical Systems International AG, Cham (CH)

(72) Inventors: Daniel Morf, Buch am Irchel (CH); Martin Amstutz, Doettingen (CH)

(73) Assignee: VARIAN MEDICAL SYSTEMS INTERNATIONAL AG, Cham (CH)

( * ) Notice: Subject to any disclaimer, the term of this patent is extended or adjusted under 35 U.S.C. 154(b) by 498 days.

(21) Appl. No.: 16/054,543

(22) Filed: Aug. 3, 2018

(65) Prior Publication Data

US 2020/0038687 A1 Feb. 6, 2020

(51) Int. Cl.
*A61N 5/00* (2006.01)
*A61N 5/10* (2006.01)

(52) U.S. Cl.
CPC ......... *A61N 5/1049* (2013.01); *A61N 5/1039* (2013.01); *A61N 5/1067* (2013.01); *A61N 5/1069* (2013.01); *A61N 2005/1061* (2013.01); *A61N 2005/1087* (2013.01)

(58) Field of Classification Search
CPC ...................................................... A61N 5/10
See application file for complete search history.

(56) References Cited

U.S. PATENT DOCUMENTS

| 5,140,162 A * | 8/1992 | Stettner ................. G01T 1/28 250/370.09 |
| 2005/0161744 A1* | 7/2005 | Frapreau ............. H01L 29/0615 257/368 |
| 2011/0006212 A1 | 1/2011 | Shchory et al. |
| 2012/0193545 A1 | 8/2012 | Tkaczyk et al. |
| 2016/0121139 A1* | 5/2016 | Da Silva Rodrigues ................... A61N 5/1071 600/1 |
| 2018/0199904 A1 | 7/2018 | Ganguly et al. |

FOREIGN PATENT DOCUMENTS

WO WO 2015189601 A1 12/2015

OTHER PUBLICATIONS

European Extended Search Report dated Dec. 12, 2019 for corresponding EP Patent Application No. 19189403.9.

* cited by examiner

*Primary Examiner* — Dani Fox
(74) *Attorney, Agent, or Firm* — Duane Morris LLP

(57) ABSTRACT

An imager includes: an array of imager elements configured to generate image signals based on radiation received by the imager; and circuit configured to perform readout of image signals, wherein the circuit is configured to be radiation hard. An imager includes: an array of imager elements configured to generate image signals based on the radiation received by the imager; and readout and control circuit coupled to the array of imager elements, wherein the readout and control circuit is configured to perform signal readout in synchronization with an operation of a treatment beam source.

31 Claims, 6 Drawing Sheets

IMAGERS IN RADIATION THERAPY ENVIRONMENT

FIELD

The field of the application relates to radiation treatment, and more particularly, to imagers for use in a radiation therapy environment.

BACKGROUND

The trend in radiation therapy is toward hypo-fractionated treatment protocols and online adaptive planning. Such treatments may deliver the entire dose in only 1-5 fractions. These treatment protocols make the accurate positioning of the patient very important. Moreover, the supervision during the actual treatment requires constant verification of the patient's position. One technique to monitor patient movements and patient positions during treatment utilizes imagers and kilovoltage (kV) x-ray. This requires an imager and an x-ray source to be at extended positions (i.e., extended from their storage or non-use positions) during the course of treatment. The treatment beam generates a substantial amount of scatter radiation. As a consequence, any device in the radiation treatment environment, such as an extended imager, can receive a high dose of radiation. While the x-ray source is insensitive to scattered radiation, an imager is not. An imager has complex electronics that may be deteriorated or damaged by high doses of radiation over time. An imager may not withstand total doses greater than 10-12 kRad.

In addition, the scattered radiation from the treatment beam may generate image artifacts on a kV imager. The treatment beam is pulsed, with a duty cycle in the order of 1:500 (or 0.2%, corresponding to 5 µs pulse width and 2.5 ms pulse period). Therefore, the dose and the associated scatter radiation are delivered in short and discrete portions. This scattered radiation dose creates line artifacts on images output by the kV imager. The line artifacts are undesirable because they make image processing difficult. The line artifacts are also undesirable because they may cause inaccurate results output by image-based algorithms. For example, if an image-based algorithm for patient positioning (which positioning is based on an image from the kV imager) receives an image with line artifacts as input, the algorithm may output a patient position that is inaccurate as a result of the line artifacts presented in the image.

SUMMARY

In some embodiments, an imager (e.g., kV imager) that is designed to be radiation hard is provided. This allows the imager to be extended from its storage or non-use position during the whole treatment, and enables patient position monitoring, or even patient or target tracking during treatment using images acquired by the imager. In one implementation, every electrical component, including the readout and control circuit in the imager is configured to withstand a minimum of 80 kRad, and more preferably a minimum of 90 kRad, and even more preferably a minimum of 100 kRad, for a specified imager life time (e.g., a minimum of 4 years).

The imager with the radiation hard design described herein is advantageous compared to current imagers. Current imagers on the market may withstand radiation exposures of about 12-15 kRad. If the imager were left at the extended position during the treatment, the lifetime would be significantly shortened due to the high amount of scatter radiation it would receive.

The imager with the radiation hard design described herein is also advantageous over imagers that use radiation shielding. The scatter radiation from the treatment radiation has a substantial amount of high energy components in it. Shielding high energy radiation may require thick and heavy materials to be incorporated into the design of the imager. The robotic arms, which move the imager, may also need to be designed to work with this additional load due to radiation shielding. In some embodiments, the imager with the radiation hard design described herein does not need any radiation shielding. In other embodiments, such imager may optionally include radiation shielding to shield at least some radiation resulting from the delivery of treatment beam. Such shielding may improve the life time of the imager.

In some embodiments, the readout of the imager described herein is synchronized to the treatment beam pulses to significantly reduce or eliminate line and banding artifacts. Without such synchronization, the line and banding artifacts would occur at random positions in an image outputted by the imager. This would make it very difficult to remove the artifacts by, for example, the use of a software algorithm. In the case of real-time tracking of patient or target position based on images from the imager, it may be impossible or very difficult to use a software algorithm to perform real-time correction on all of the images. The readout synchronization described herein allows the imager to create images (e.g., read-time images) that are free of line-artifacts. Also, in some embodiments, the signal readout of the imager may be suspended during the treatment beam pulse to further improve the quality of the images outputted by the imager.

An imager may include: an array of imager elements configured to generate image signals based on radiation received by the imager; and circuit configured to perform readout of image signals, wherein the circuit is configured to be radiation hard.

Optionally, the circuit is configured to withstand at least 100 kRad of radiation.

Optionally, the circuit is configured to withstand at least 500 kRad of radiation.

Optionally, the imager is configured to remain fully functional even after the imager has been exposed to radiation resulting from up to 18 MV treatment beam with parameters of 100 kRad and 600 Monitor Units (Mu)/min.

Optionally, the circuit comprises a readout and control circuit coupled to the array of imager elements, wherein the readout and control circuit is radiation hard.

Optionally, the circuit comprises a gate driver, wherein the gate driver is radiation hard.

Optionally, the circuit of the imager comprises a commercial component that is not marketed as radiation hard, but has been tested as meeting certain radiation hardness requirement.

Optionally, the circuit of the imager comprises a commercial component that is marketed as radiation hard.

Optionally, the circuit of the imager comprises a component that is custom-designed to meet certain radiation hardness requirement.

Optionally, the imager further comprises radiation shielding.

Optionally, the circuit comprises a readout and control circuit coupled to the array of imager elements, wherein the readout and control circuit is configured to perform signal readout in synchronization with an operation of a treatment beam source.

Optionally, the readout and control circuit is configured to start the signal readout for an image frame at a pre-determined time or within a predetermined time period with respect to a treatment beam pulse.

Optionally, the readout and control circuit is configured to suspend the signal readout when the treatment beam source is delivering a treatment beam pulse or multiple treatment beam pulses.

Optionally, the readout and control circuit is configured to perform signal readout for one or more lines of the imager during a treatment session when the treatment beam source is not delivering treatment energy, and to suspend signal readout for another line of the imager when the treatment beam source is delivering treatment energy.

Optionally, the treatment beam source is configured to hold off a delivery of a treatment beam pulse or multiple treatment beam pulses for a beam hold period.

Optionally, the beam hold period is long enough to allow the imager to reset the array of imager elements, receive imaging dose, and readout the image signals.

Optionally, the circuit comprises a layout configured to provide radiation hardness.

Optionally, the circuit comprises an edge-less transistor, an enclosed layout transistor (ELT), at least two transistors with guard rings between the two transistors, or any combination of the foregoing.

Optionally, the array of imager elements is configured to generate image signals based on light signals provided by a scintillator layer.

Optionally, the array of imager elements is configured to generate image signals based on charges provided by a conversion layer.

Optionally, the array of imager elements is configured to generate image signals based on photon counting.

Some embodiments of an imager may include: an array of imager elements configured to generate image signals based on the radiation received by the imager; and circuit coupled to the array of imager elements, wherein the circuit is configured to perform signal readout in synchronization with an operation of a treatment beam source.

Optionally, the circuit is configured to start the signal readout for an image frame at a pre-determined time or within a predetermined time period with respect to a treatment beam pulse.

Optionally, the circuit is configured to suspend the signal readout when the treatment beam source is delivering a treatment beam pulse.

Optionally, the circuit is configured to perform signal readout for one or more lines of the imager during a treatment session when the treatment beam source is not delivering treatment energy, and to suspend signal readout for another line of the imager when the treatment beam source is delivering treatment energy.

Optionally, the treatment beam source is configured to hold off a delivery of a treatment beam pulse for a beam hold period.

Optionally, the beam hold period is long enough to allow the imager to reset the array of imager elements, receive imaging dose, and readout the image signals.

Optionally, the circuit is configured to be radiation hard.

Optionally, the circuit comprises readout and control circuit coupled to the array of imager elements, wherein the readout and control circuit is radiation hard.

Optionally, the circuit comprises a gate driver, wherein the gate driver is radiation hard.

Optionally, the array of imager elements is configured to generate the image signals based on light signals provided by a scintillator layer.

Optionally, the array of imager elements is configured to generate the image signals based on charges provided by a conversion layer.

Optionally, the array of imager elements is configured to generate image signals based on photon counting.

Optionally, the circuit is configured to perform signal readout in synchronization with the operation of the treatment beam source to prevent a band artifact, a dark line artifact, a bright line artifact, or any combination of the foregoing.

Other and further aspects and features will be evident from reading the following detailed description.

DESCRIPTION OF THE DRAWINGS

The drawings illustrate the design and utility of some embodiments, in which similar elements are referred to by common reference numerals. These drawings are not necessarily drawn to scale. In order to better appreciate how the above-recited and other advantages and objects are obtained, a more particular description of some embodiments will be rendered, which are illustrated in the accompanying drawings. These drawings depict only exemplary embodiments and are not therefore to be considered limiting in the scope of the claims.

DETAILED DESCRIPTION

Figure 1:
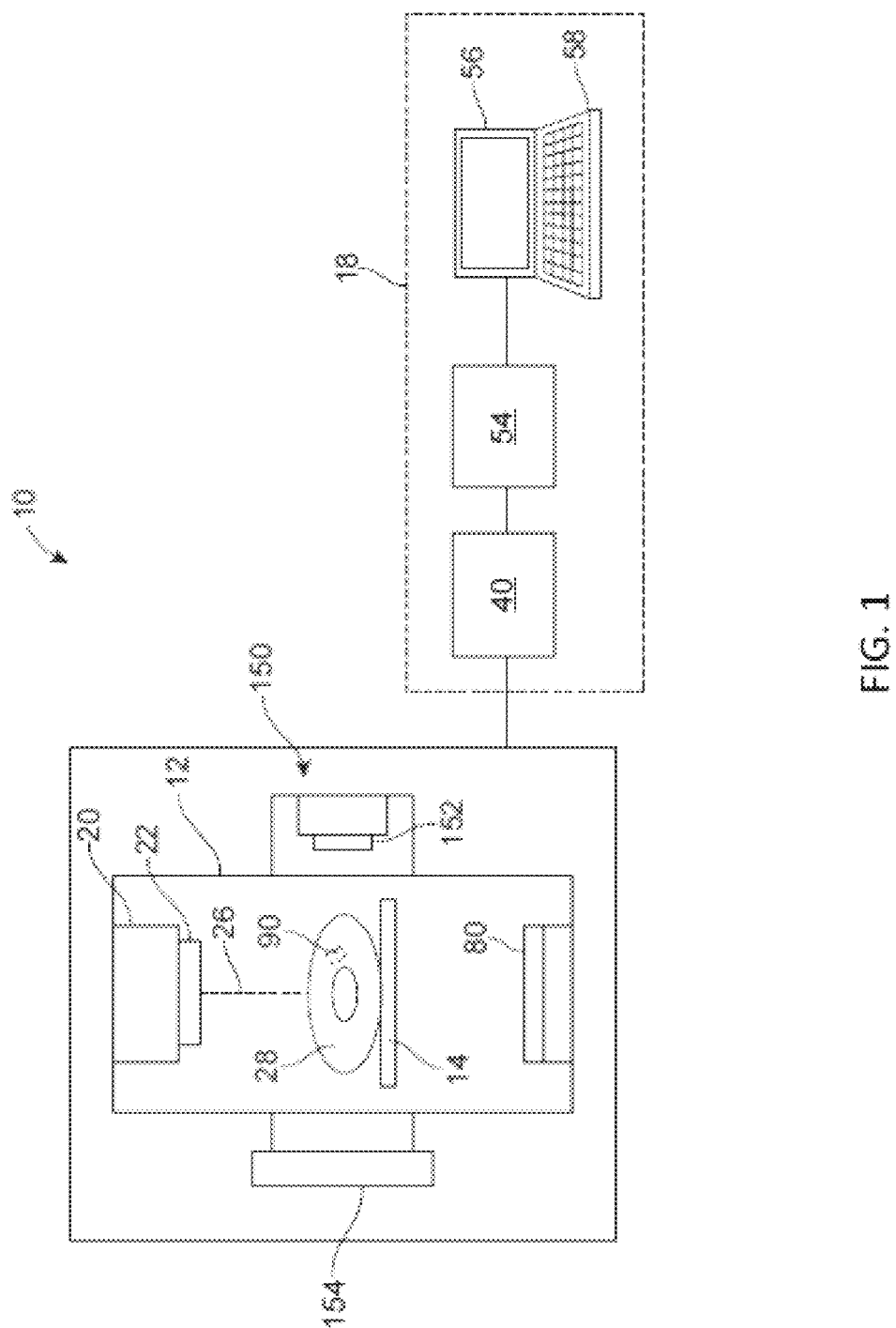
FIG. 1 illustrates a radiation system having an imager in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment need not have all the aspects or advantages shown. An aspect or an advantage described in conjunction with a particular embodiment is not necessarily limited to that embodiment and can be practiced in any other embodiment even if not so illustrated, or if not so explicitly described.

FIG. 1 illustrates a radiation system 10. The system 10 is a treatment system that includes a gantry 12, a patient support 14 for supporting a patient 28, and a control system 18 for controlling an operation of the gantry 12. The gantry 12 is in a form of an arm, but in other embodiments, the gantry 12 may have other forms (such as a ring form, etc.). The system 10 also includes a radiation source 20 that projects a beam 26 of radiation towards a patient 28 while the patient 28 is supported on support 14, and a collimator system 22 for controlling a delivery of the radiation beam 26. The collimator 22 may be configured to adjust a cross sectional shape of the beam 26. The radiation source 20 can be configured to generate a cone beam, a fan beam, or other types of radiation beams in different embodiments.

As shown in FIG. 1, the system 10 also includes an imager 80, located at an operative position relative to the source 20 (e.g., under the support 14). In the illustrated embodiments, the radiation source 20 is a treatment radiation source for providing treatment energy. In such cases, the treatment energy may be used by the imager 80 to obtain images. In order to obtain imaging using treatment energies, the imager 80 is configured to generate images in response to radiation having treatment energies (e.g., MV imager). In other embodiments, in addition to being a treatment radiation source, the radiation source 20 can also be a diagnostic radiation source for providing diagnostic (imaging) energy for imaging purpose. In further embodiments, the system 10 may include the radiation source 20 for providing treatment energy, and one or more other radiation sources for providing diagnostic energy. In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. Also, in some embodiments, a treatment energy may be 6 MV or higher (e.g., 18 MV, 25 MV, etc.). In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. In other embodiments, the radiation source 20 may be configured to generate radiation at other energy ranges.

In the illustrated embodiments, the control system 18 includes a processing unit 54, such as a computer processor, coupled to a control 40. The control system 18 may also include a monitor 56 for displaying data and an input device 58, such as a keyboard or a mouse, for inputting data. The operation of the radiation source 20 and the gantry 12 are controlled by the control 40, which provides power and timing signals to the radiation source 20, and controls a rotational speed and position of the gantry 12, based on signals received from the processing unit 54. In some cases, the control 40 may also control the collimator system 22 and the position of the patient support 14. In addition, in some embodiments, the control 40 may be configured to control an operation of the imager 80. Although the control 40 is shown as a separate component from the gantry 12 and the processor 54, in alternative embodiments, the control 40 can be a part of the gantry 12 or the processing unit 54.

In some embodiments, the system 10 may be a treatment system configured to deliver treatment radiation beam towards the patient 28 at different gantry angles. During a treatment procedure, the source 20 rotates around the patient 28 and delivers a treatment radiation beam from different gantry angles towards the patient 28. While the source 20 is at different gantry angles, the collimator 22 is operated to change the shape of the beam to correspond with a shape of the target tissue structure. For example, the collimator 22 may be operated so that the shape of the beam is similar to a cross sectional shape of the target tissue structure. In another example, the collimator 22 may be operated so that different portions of the target tissue structure receive different amount of radiation (as in an IMRT procedure).

In the illustrated embodiments, the system 10 also includes an imaging device 150 having an imaging source 152 and an imager 154. The imaging device 150 is configured to obtain one or more images of an internal part of the patient 28. The image(s) obtained by the imaging device 150 may be used to setup the patient 28, monitor a position of the patient 28, track a target within the patient 28, or any combination of the foregoing. In some cases, the imaging device 150 may be configured to obtain images of an internal fiducial 90 of the patient 28. The internal fiducial 90 may be an internal structure inside the patient 28. In some embodiments, the internal structure may move in correspondence (e.g., in sync) with a target of the patient 28 that is desired to be treated. In such cases, the internal structure may be used as a surrogate for determining a position and/or movement of the target during treatment of the patient 28, and motion management based on the surrogate may be employed in some cases. Thus, the internal fiducial 90 may be imaged by the imaging device 150 (and/or by the radiation source 20 and imager 80) that functions as a position monitoring system during a treatment of the patient 28. By means of non-limiting examples, the internal fiducial 90 may be an anatomical surrogate, such as bony structure, a vessel, a natural calcification, or any other items in a body. As discussed, the imaging device 150 and/or the imager 80 may also be used for target tracking and/or patient positioning. In some embodiments, the control 40 may be configured to control an operation of the imaging device 150. For example, the control 40 may provide one or more control signals to activate the imaging source 152, and/or to operate a readout and control circuit in the imager 154.

In some embodiments, the imaging device 150 may be an x-ray device. In such cases, the imaging source 152 comprises a radiation source. In other embodiments, the imaging device 150 may have other configurations, and may be configured to generate images using other imaging techniques. For example, in other embodiments, the imaging device 150 may be an ultrasound imaging device, a MRI device, a tomosynthesis imaging device, or any of other types of imaging devices. Also, in the above embodiments, the imaging device 150 is illustrated as being integrated with the treatment machine. In other embodiments, the imaging device 150 may be a separate device that is separate from the treatment machine. In addition, in some embodiments, the imaging device 150 may be a room-based imaging system or a couch based imaging system. In either case, the imaging device 150 may provide any form of imaging, such as x-ray imaging, ultrasound imaging, MRI, etc. Furthermore, in other embodiments, the imaging device 150 may provide in-line imaging in the sense that it may be configured to acquire images along the same direction as the treatment beam. For example, a dual-energy source (integrating the treatment source 20 and the imaging source 152) may be provided to provide imaging energy for generating an image, and to provide treatment energy to treat a patient along the same direction. In such cases, the imager 154 may replace the imager 80, or may be integrated with the imager 80 to form a hybrid-imager, which is configured to provide kV and MV imaging. In still further embodiments, the imaging device 150 and/or the imaging device 80 may be configured to provide dual energy imaging and any form of energyresolved imaging to increase contrast in x-ray images. For example, a first part of an image may be generated using a first energy, and a second part (e.g., a more relevant part that includes a target) of the same image may be generated using a second energy that is higher than the first energy. As a result, the second part of the image may have higher contrast compared to the first part. However, the overall dose involved in generating the whole image may be reduced compared to the situation in which the entire image is generated using the second energy.

Imager with Radiation Hard Feature

Figure 2:
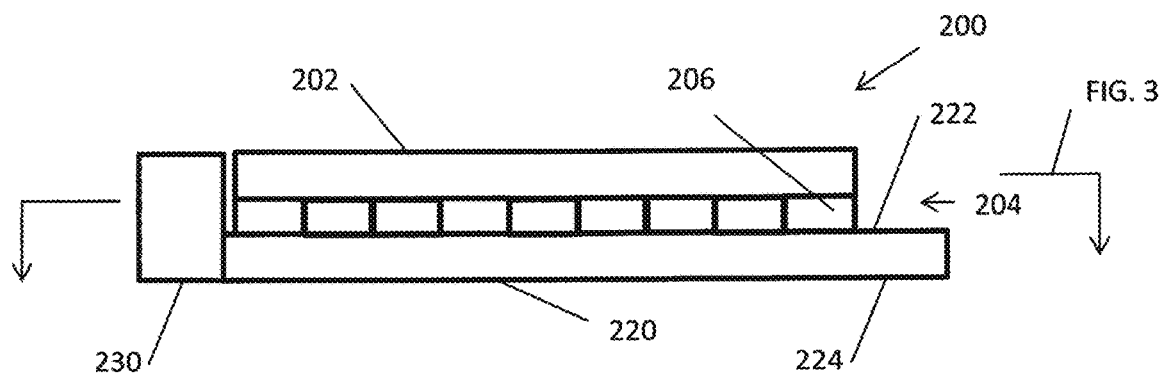
FIG. 2 illustrates an imager.

FIG. 2 illustrates an imager 200 with radiation hardness feature in accordance with some embodiments. The imager 200 may be implemented as imager 154 or imager 80 of FIG. 1 in some embodiments. The imager 200 is configured to receive imaging radiation from an imaging source (e.g., source 152 or 20), and generates image signals in response to the imaging radiation. The imager 200 includes a layer 202 of scintillator (or scintillator layer 202) configured to receive the imaging radiation, and to generate light in response to the imaging radiation. The scintillator layer 202 may be pixelated or non-pixelated. The imager 200 also includes an array 204 of imager elements 206. Each imager element 206 is configured to generate image signal(s) in response to light received from the scintillator layer 202.

In some embodiments, each imager element 206 may include one or more amorphous silicon (a:Si) detectors. Also, in some embodiments, the imager element 206 may be implemented using a photodiode. In this specification, the term "photodiode" refers to one or more electrical circuit element(s) on a detector pixel that are associated with converting photon energy into electrical signals. This can include, but is not limited to, photodiode(s), switching transistor(s), amplification transistor(s), direct conversion element, indirect conversion elements, photon counting elements, or a combination thereof. In some embodiments, the electrical circuit element(s) of the imager element 206 is designed (e.g., being made from radiation resistant material, and/or having a configuration) to be radiation hard. The scintillator layer 202 is configured to receive radiation and generate photons in response to the radiation. The photodiode element of the imager element 206 is configured to generate electrical signals in response to the photons provided from the scintillator layer 202. The electrical signals are then read out by readout and control circuit 230, and are digitized to form an image. In the illustrated embodiments, the readout and control circuit 230 is designed (e.g., being made from radiation resistant material, and/or having a radiation resistant configuration) to be radiation hard. In some embodiments, the readout and control circuit 230 is communicatively connected to the control 40, or another separate control, for controlling an operation of the readout and control circuit 230.

In some embodiments, signals from each photodiode of each imager element 206 form a pixel in an image. In other embodiments, a binning circuit is optionally provided to combine the signals from two or more photodiodes of two or more respective imager elements 206 to form each pixel in the image. For example, the binning circuit of the imager 200 may be configured to provide 2×2 binning, 3×3 binning, 4×4 binning, 1×2 binning, 1×4 binning or binning of other number of pixels. In some embodiments, the binning circuit may be designed (e.g., being made from radiation resistant material, and/or having a configuration) to be radiation hard. For example, the binning circuit may include circuit components configured to withstand radiation. The binning circuit may be implemented as a part of the access and control circuit 230 in some embodiments.

As shown in FIG. 2, the imager 200 further includes a glass substrate 220, wherein the array 204 of imager elements 206 is secured to the glass substrate 220. In the illustrated embodiments, the glass substrate 220 has a first side 222 and an opposite second side 224, wherein the first side 222 is closer to a radiation source than the second side 224. In some embodiments, the array 204 of imager elements 206 is located closer to the first side 222 of the glass substrate 220 than the second side 224. In other embodiments, the substrate 220 may be made from materials that are different from glass. For example, in other embodiments, the substrate 220 may be made from plastic.

Figure 3:
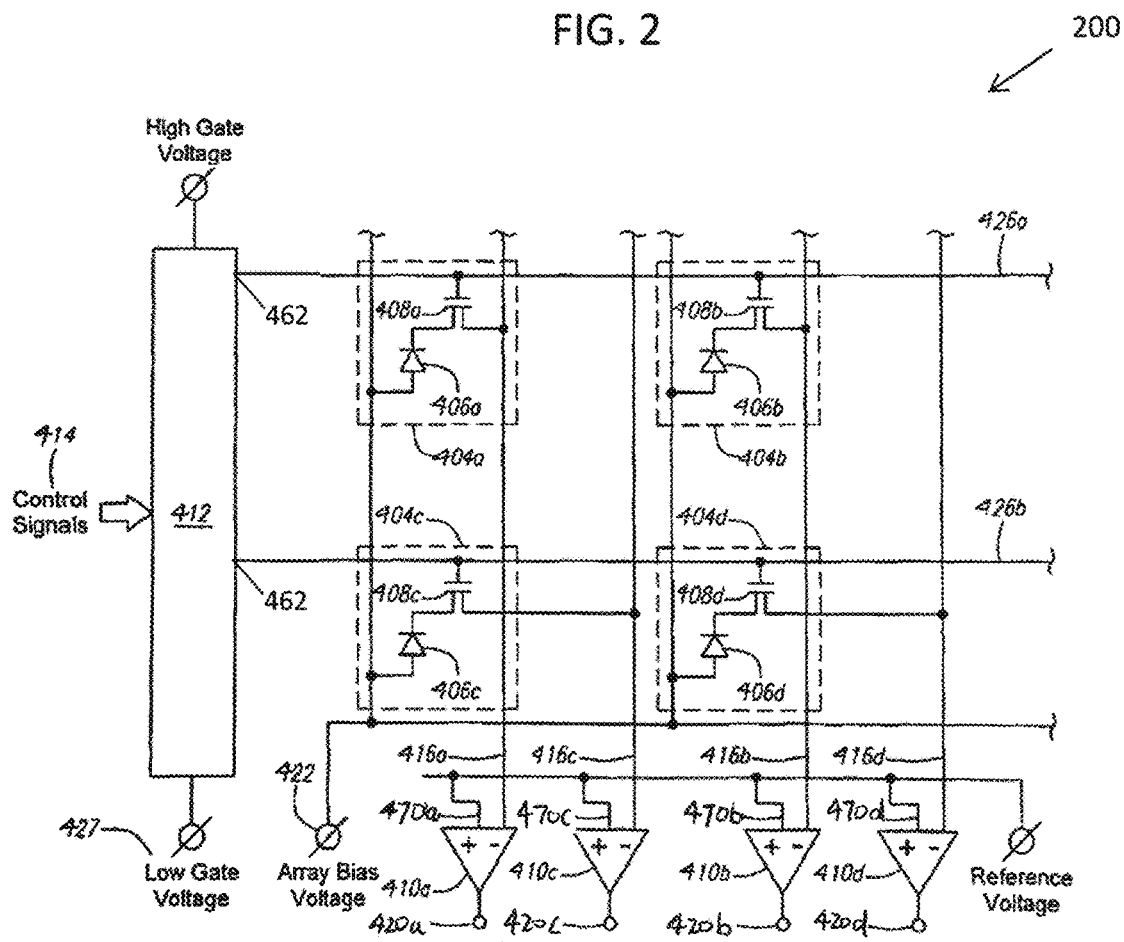
FIG. 3 illustrates exemplary electrical components of the imager of FIG. 2.

FIG. 3 depicts one exemplary configuration of electrical components for the imager 200 in accordance with some embodiments. The imager 200 includes a plurality of imager elements 404 (i.e., 404a-404d) having respective photodiodes 406 (i.e., 406a-406d). The photodiodes 406 form part of the imager element 206 of FIG. 2. Each of the photodiodes 406 is configured to generate an electrical signal in response to a light input. The photodiode 406 receives light input from the scintillator layer 202 that generates light in response to x-rays. The photodiodes 406 are connected to an array bias voltage 422 to supply a reverse bias voltage for the imager elements 404. A transistor 408 (such as a thin-film N-type FET) functions as a switching element for each imager element 404. When it is desired to capture image data from the imager elements 404, control signals 414 are sent to a gate driver 412 to "select" the gate(s) of transistors 408. The gate driver 412 is connected to a low gate voltage 427 and high gate voltage source that drives the gate control lines 426a, 426b. In particular, the gate driver 412 provides drive signals to the gate control lines 426a, 426b. In response to the drive signals, electrical signals from the photodiodes 406 are passed through lines 416 (i.e., 416a-416d) to corresponding charge amplifiers 410a-410d, which are connected to a reference voltage via lines 470a-470d, respectively. The output of the charge amplifiers 410 is sent via outputs 420 (e.g., 420a-420d) to a "sample and hold" stage for further image processing/display. In one embodiment, the gate driver 412 is a part of the readout and control circuit 230 of FIG. 2, which may be located along one or more side(s) of the imager 200. The readout and control circuit 230 may include one or more of the components shown in FIG. 3, such as the gate driver 412, the charge amplifiers 410, the outputs 420, gate control lines 426, lines 416, lines 470, reference voltage source and/or conductor of the reference voltage, array bias voltage and/or conductor of the array bias voltage, high and low gates voltage source and/or conductor of the high and low gates voltage, the digital control circuits, or any combination of the foregoing. In some embodiments, one or more (or all) of the above components of the readout and control circuit 230 may be radiation hard. In addition, in some embodiments, the readout and control circuit 230 may be a part of an integrated circuit, wherein a part or an entirety of the integrated circuit may be radiation hard. Such circuit may include any of the components of the readout and control circuit 230 described above, including but not limited to gate driver 412, charge amplifiers 410, digital control circuits, etc.

While FIG. 3 only shows four imager elements 404a-404d, those skilled in the art would understand that the imager 200 may include many such imager elements 404, depending upon the size and resolution of the imaging device. In addition, although only two gate control lines 426a and 426b for accessing image signals from imager elements 404 are shown, the imager 200 may include more than two gate control lines 426. In the illustrated embodiments, the gate driver 412 has multiple outputs 462 accessing respective gate control lines 426, one line at a time. In other embodiments, the gate driver 412 may be configured to access multiple (e.g., two, four, six, etc.) gate control lines 426 simultaneously. For example, each output 462 of the gate driver 412 may connect to multiple gate control lines 426 for accessing the multiple gate control lines 426 simultaneously. Such configuration allows image signals to be collected from two or more lines of imager elements 104 simultaneously, thereby increasing the signal collection process. For a given configuration of the imager 200, a signal readout time for each gate control line 426 of imager elements 404 depends on the time it takes to turn on a pixel and discharge a corresponding image signal. As such, by configuring the imager 200 to allow image signals from two or more lines of imager elements 404 to be read simultaneously or in parallel, the time it takes to readout image signals from all the lines of the imager 200 can be reduced. This in turn, improves the frame rate (i.e., number of image frames that can be generated by the imager 200 per second) of the imager 200.

It should be noted that the electrical components and the electrical layout of the imager 200 should not be limited by the example shown in FIG. 3, and that in other embodiments, the imager 200 may have electrical component(s) and/or electrical layout that is different from that shown in FIG. 3.

As discussed, the imager 200 is configured to have radiation hardness. It has been discovered that 80 kRad is approximately the dose that an imager may receive in a lifetime under normal usage when it is in the scatter beam area of a radiation beam.

Accordingly, in some embodiments, the electronics of the imager 200 is configured to withstand (i.e., the imager 200 does not break or fail) a certain minimum radiation dose (e.g, 80 kRad, 90 kRad, 100 kRad, 200 kRad, 500, kRad, or higher). In some embodiments, the imager 200 may be considered as being radiation hard if the imager 200 has no degradation of key performance parameters (e.g., dark current, sensitivity, linearity, current consumption, lag, etc.) after receiving a certain dose (e.g., 80 kRad, 90 kRad, 100 kRad, 200 kRad, 500 kRad, or higher). In further embodiments, the imager 200 may be considered as being radiation hard if it can withstand photon and neutrons radiation (e.g., it has no failure and/or no performance degradation) after being tested under the following conditions: Use 18 MV energy beam to deliver 100 kRad of radiation dose to the imager at a rate of 600 Mu/min. In other embodiments, the beam energy for testing neutron radiation hardness may have other values, such as 10 MV or higher. Also, in other embodiments, the rate of radiation delivery for testing for radiation hardness of the imager may be different from 600 Mu/min (e.g., higher or lower than 600 Mu/min).

There are various techniques to obtaining radiation hard electronics. In some embodiments, commercial components may be selected, and they can be tested for radiation hardness (e.g., to determine if they will fail after exposure to a certain amount of radiation dose). These commercial components may or may not be marketed as radiation hard. As another alternative, off the shelf components that are marketed as radiation hard may be utilized. In other embodiments, specific integrated circuits may be custom-designed such that they are radiation hard. In some embodiments, all of the electronics in the imager 200 may be (1) commercial components (not marketed as radiation hard components) that have been tested as having met certain radiation hardness requirements by the provider of the imager 200, (2) commercial components that are marketed as radiation hard, (3) custom-designed to meet certain radiation hardness requirement, or (4) any combination of the foregoing (such as (1)+(2), (1)+(2)+(3), (1)+(3), (2)+(3)).

In other embodiments, instead of, or in addition to, the above techniques for providing radiation hardness for the imager 200, electronics of the imager 200 may include a circuit layout that provides or improves radiation hardness for the imager 200.

Figure 4A:
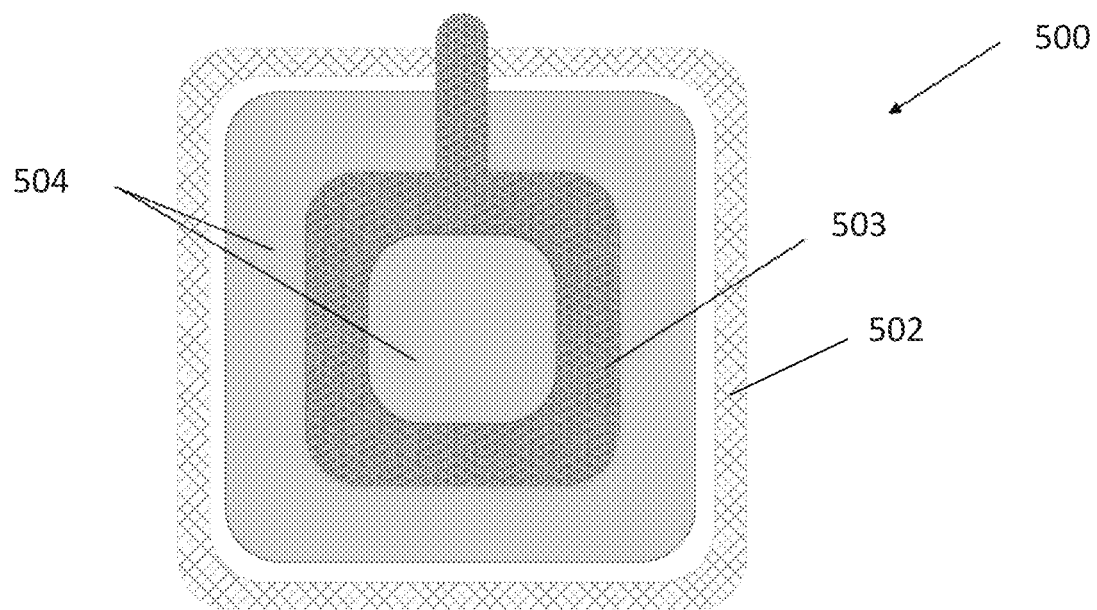
FIG. 4A illustrates an example of a transistor with guard ring and round gate.
Figure 4B:
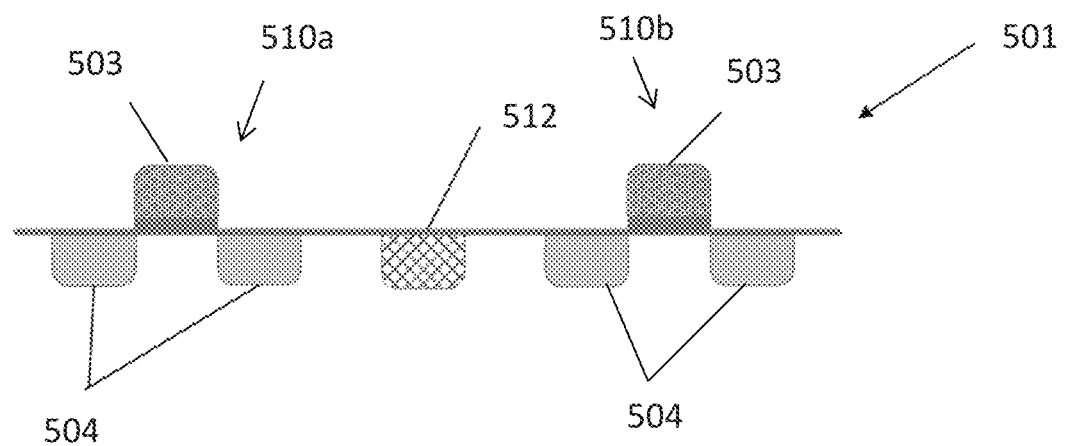
FIG. 4B illustrates a cross section of transistors with guard ring therebetween.

For example, in some embodiments, the imager 200 may include an edge-less transistor to provide radiation hardness for the imager 200. FIG. 4A illustrates an example of an edge-less transistor 500 with round or circumferential gate 503, source/drain 504, and guard ring 502, which prevents inter-device leakage. Edge-less transistor(s), such as that shown in FIG. 4A, may be utilized as a part of the electronics for the readout and control circuit 230. In one implementation, the edge-less transistor may be a NMOS enclosed-layout transistor (ELT) device, a CMOS ELT device, or it may be any type of ELT device. Due to the guard ring, deposited charges resulted from radiation cannot form a parasitic channel between the transistor 500 and an adjacent transistor (not shown). In other embodiments, other types of transistor layout may be utilized for the electronics of the readout and control circuit 230. For example, the imager 200 may include a guard ring or guard structure between transistors to provide radiation hardness for the imager 200. FIG. 4B illustrates a cross section 501 of transistors 510a, 510b with a guard ring or guard structure 512 between the transistors 510a, 510b, which may be utilized as a part of the electronics for the readout and control circuit 230. Due to the guard ring or guard structure 512, deposited charges resulted from radiation cannot form a parasitic channel between the transistors 510a, 510b.

In other embodiments, instead of, or in addition to, utilizing radiation hard components to construct the imager 200, electronics of the imager 200 may be placed further away from the scatter radiation. For example, after the imager 200 is extended from its "home" position to obtain image(s) of the patient, the imager 200 may be moved back to its "home" position. Alternatively, instead of moving all the way back to the "home" position, the imager 200 may be simply moved further away from the radiation scatter area. For example, the imager 200 may remain deployed from its "home" position, but may be moved further away from the isocenter when it is not being used to obtain image(s) of the patient.

Also, in other embodiments, in addition to utilizing radiation hard components to construct the imager 200, radiation shielding may be added to further protect the electronics of the imager 200. Since the treatment beam has very high energy (e.g., it has megavolt radiation), utilizing only shielding to shield such high radiation would require a thick and heavy shielding, and would consume a lot of space. However, because the electronics of the imager 200 are already designed to be radiation hard, a full shielding is not required for such imager 200. In such cases, the imager 200 may be provided with a shielding that is only a fraction of that required to block all of the high energy scattered radiation. For example, if a full shielding required to protect non-radiation hard electronics of the imager has a 3 inch thickness, then a partial shielding of 0.5 inch thickness may be provided for the imager constructed with radiation hard electronics. Accordingly, in some embodiments, the radiation hardness requirement may be reduced if some shielding is provided for the imager 200.

During use of the imager 200, the imager 200 and the radiation source 152 are moved from their "home" (or storage) positions to their operative positions so that they are on opposite sides of the patient. At such operative positions, the scintillator layer 202 can receive imaging radiation from the radiation source 152. As discussed, the scintillator layer 202 receives the imaging radiation that has passed through the patient, and generates light photons in response to the received radiation. The photons are detected by the imager elements 206. The imager elements 206 generate electrical signals (image signals) in response to the photons detected by the imager elements 206. In one mode of operation, the electrical signals from the respective imager elements 206 form respective pixels of an image. In another mode of operation, the electrical signals from some of the imager elements 206 are combined, e.g., via a binning circuit, to form a pixel of an image. In some cases, the binning circuit may be considered to be a part of the access and control circuit 230. The image signals may be transmitted to a device, such as a processor for determining an image based on the image signals, and/or to a medium for storage.

In some embodiments, after the imager 200 has been used to capture image(s) of the patient, the imager 200 may remain deployed from its "home" position. Because the imager 200 is radiation hard, the imager 200 is not required to be moved back to its "home" position to protect the imager 200 from damaging radiation. Alternatively, the imager 200 may be moved further away from the isocenter while remain deployed, so that the imager 200 receives less harmful effect due to scattered radiation.

Also, in some embodiments, the imager 200 may remain deployed and may be used to substantially continuously obtain real-time images of the patient 28 during the treatment session. For example, the imager 200 may be configured to obtain a sequence of images that are at a frequency of 1 image per second, or more preferably 3 images per second, or even more preferably 5 images per second. Because the imager 200 is radiation hard, it can be remained deployed to perform this type of real-time continuous imaging, and the imager 200 (e.g., the electronics in the access and control circuit 230) will not be damaged due to exposure of scattered radiation resulted from the high energy treatment beam.

In the above embodiments, the imager elements 206 are described as generating image signals based on light signals received from the scintillator layer 202. In other embodiments, the imager elements 206 may be other types of imager elements that generate image signals based on radiation received by the imager 200. For example, in other embodiments, the imager elements 206 may be configured to generate image signals based on charges provided by a conversion layer. In such cases, the conversion layer is configured to generate electron-hole-pairs based on radiation received by the imager 200. Based on the electron-hole-pairs (charges), the imager elements 206 then generates image signals. In further embodiments, the imager elements 206 may be configured to generate image signals based on photon counting. In such cases, photon counter may be provided for each imager element 206. The photon counter counts number of photons generated based on radiation received by the imager 200. Each imager element 206 then generates image signal(s) based on the number of photons counted by the corresponding photon counter.

Image Artifacts Due to Treatment Beam Pulses being Asynchronous to Image Readout In some cases, operation of an imager (such as the imager 200) may result in certain image artifacts due to the fact that the treatment beam pulses are not synchronized with the image readout of the imager. For example, the treatment beam pulses may occur periodically at a first rate, and the readout of the imager 200 may be performed at a second rate different from the first rate. This results in the readout of the imager 200 being asynchronous to the treatment beam pulse. Between the previous readout cycle of the imager 200 and the current readout cycle, the imager 200 integrates received dose (i.e., the scattered dose from the treatment beam). As a consequence, not every line of the imager 200 has integrated the same amount of dose from the treatment beam pulses scatter. Some lines of the imager 200 may receive more scattered dose than others, resulting in horizontal bands (or lines) artifacts. Because the readout is not synchronized, the position of the horizontal artifacts changes from image to image, and they may be difficult to be corrected using existing image processing techniques.

Figure 5A:
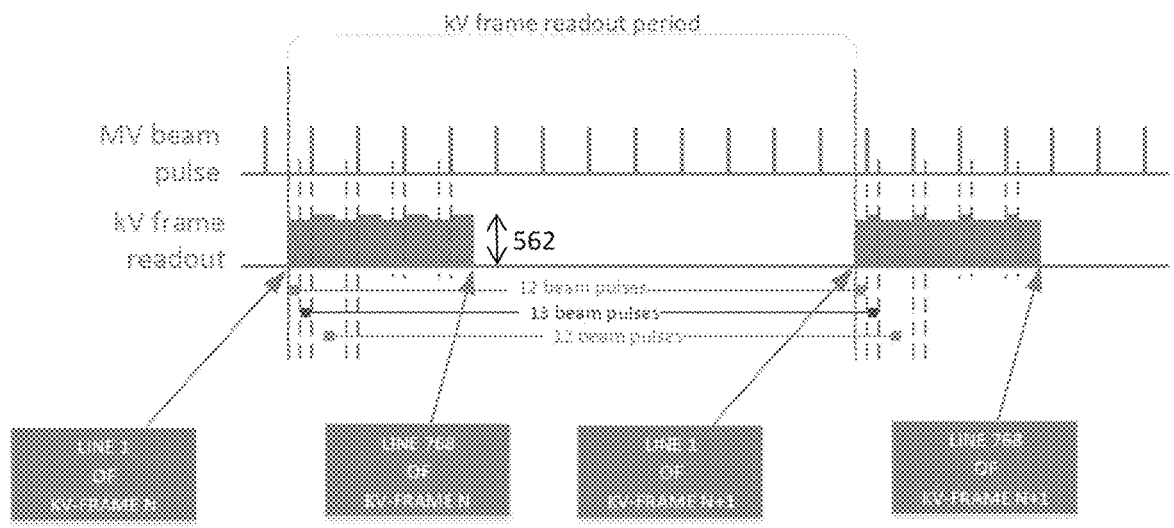
FIG. 5A is a diagram illustrating MV beam pulses being asynchronous to the kV image readout.
Figure 6:
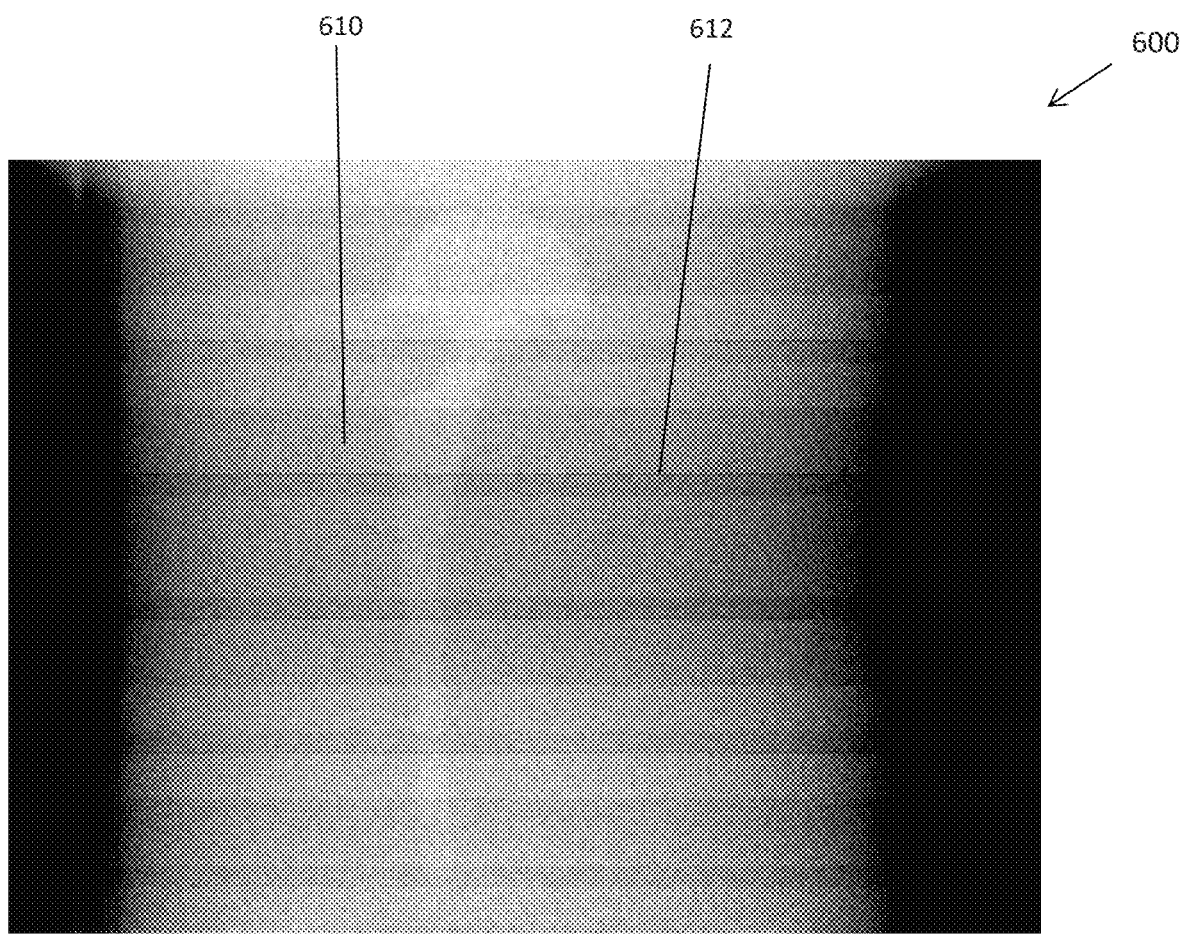
FIG. 6 illustrates an example of a kV image that includes horizontal bands and lines due to MV scatter.

FIG. 5A is a diagram illustrating the above concept, particularly showing treatment beam pulses being asynchronous to the image readout of an imager (e.g., the imager 200). As discussed, the treatment beam pulses are asynchronous to the image readout of the imager 200. As shown in the figure, the MV scatter (that is present only during the MV treatment beam pulse) is detected by the imager 200, which generates electrical signals in response to the detected scatter. The signals are integrated by the imager 200. The heights 562 of the kV frame lines shown in the figure represent the amount of MV scatter signal received in different lines of the imager 200. Note that the imager (pixels) integrates all the charge that has been seen between two consecutive frame readouts. For example, a pixel in line 1 integrates all the scatter (MV pulse) seen between "LINE 1 OF kV-FRAME N" and "LINE 1 OF kV-FRAME N+1". Thus, some part (lines) of the kV frame n+1 has seen the scatter of twelve beam pulses, and some have seen the scatter of thirteen beam pulses, in the example shown. This will show up in the image as horizontal bands with different contrasts or intensities. FIG. 6 illustrates an example of a kV image 600 that includes horizontal bands 610 due to MV scatter. In the kV image 600, there are also thin black lines 612. Each thin black line 612 has a thickness of one pixel or multiple pixels, and it is caused by the line of pixels being activated (TFT on) at the same time as the treatment beam pulse is being delivered.

Figure 5B:
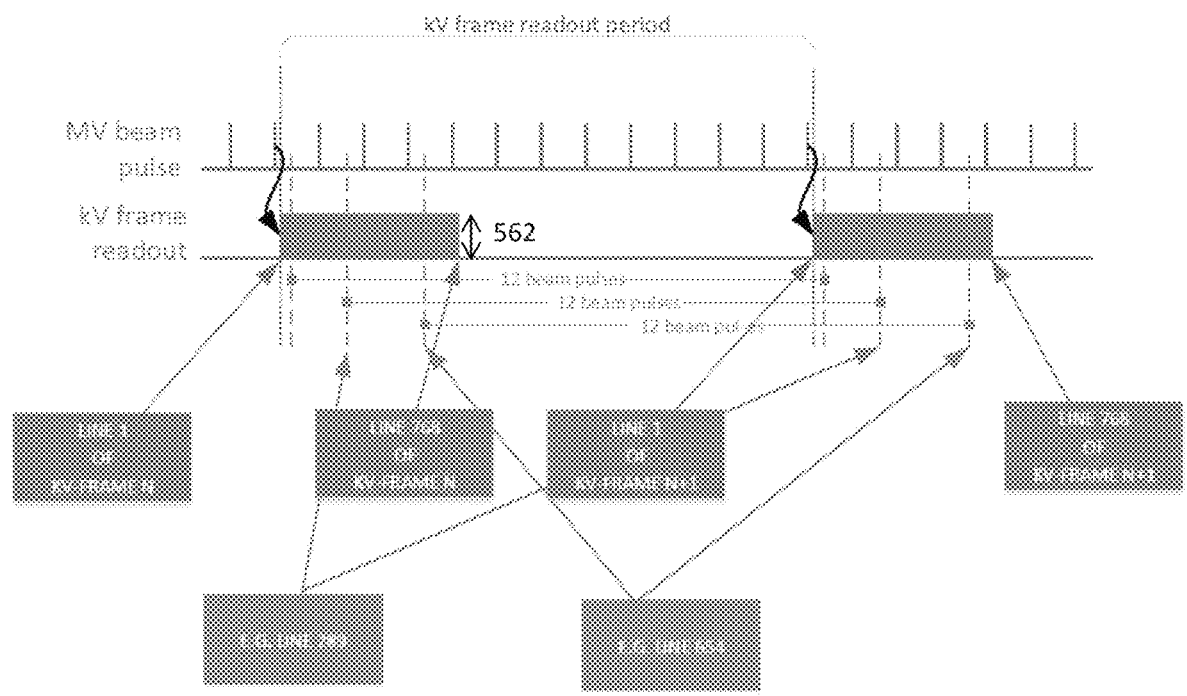
FIG. 5B is a diagram illustrating MV beam pulses being synchronous with the kV image readout.

In some embodiments, the above "band" artifact problem may be addressed by configuring the line readout of the imager 200 so that it is synchronized with the treatment beam pulses. FIG. 5B is a diagram illustrating MV beam pulses being synchronous with the kV image readout. As shown in the figure, the readout of the kV image signals is synchronized with the treatment beam pulses, so that there are always twelve scatter pulses (from the treatment beams) between corresponding lines of two consecutive image frames. For example, there are twelve scatter pulses between the readout of line 289 in the kV-FRAME N, and the readout of line 289 (i.e., the same line) in the KV-FRAME N+1. There are also twelve scatter pulses between the readout of line 654 in the kV-FRAME N, and the readout of line 654 in the KV-FRAME N+1. Accordingly, the imager always integrates twelve scatter pulses from the treatment beams between two consecutive image frames for each of the pixel lines. As a result, the heights 562 of the kV frame lines shown in the figure (representing the amount of MV scatter signal received in different lines of the imager 200) are the same, thereby eliminating the band artifacts.

One technique of achieving the above synchronization is to ensure that the kV frame readout always begins at a certain pre-determined time, or within a pre-determined time period, with respect to a beam pulse. For example, the readout and control circuit 230 may be configured to start the signal readout for an image frame at a pre-determined time or within a predetermined time period with respect to a treatment beam pulse. The curved arrows in the figure represent an example of such synchronization. In some embodiments, the readout and control circuit 230 may be configured to detect a condition indicating a treatment beam pulse or an imminent occurrence of a treatment beam pulse, and use such detected condition as a trigger to begin a readout of an image frame. This ensures that the kV readout for an image frame always begins at the same time, or within the same time duration, with respect to a treatment beam pulse. In other embodiments, the readout and control circuit 230 may be configured to receive a signal indicating an occurrence (or imminent occurrence) of a treatment beam pulse, and use such signal as a trigger to begin a readout of an image frame.

In some embodiments, the above "line" artifact problem may be addressed by also configuring the line readout of the imager 200 so that it is synchronized with the treatment beam pulses. For example, the line readout of the imager 200 may be suspended when a treatment beam pulse occurs. In one implementation, the control (e.g., control 40 of FIG. 1) of the treatment machine may be configured to send a signal to the imager 200 (or to a control controlling an operation of the imager 200) to inform the imager 200 (or its control) that a treatment beam pulse is about to occur. The imager 200 then suspends the line readout in response to the signal. The imager 200 may be configured to resume the line readout after a prescribed period of time. Alternatively, the treatment machine may be configured to send another signal to the imager 200 to cause the imager 200 to resume the line readout after the beam pulse has occurred. Accordingly, the line artifact may be removed by making sure that a line of pixels is not activated at the same time as a treatment beam pulse is being delivered.

In other embodiments, if the imager 200 is synchronized to the treatment beam, the treatment beam may be held-off for a short amount of time (e.g., 100-200 ms) to allow the imager 200 to acquire the kV image during this hold-off period. The beam hold period may be designed to be long enough to reset the imager elements, apply the kV pulse, and readout out the final image. This approach may prolong the treatment time because of the required hold-off time for the treatment beam, but it is an alternative solution. In one implementation, the imager 200 (or a control controlling the operation of the imager 200) may be configured to send a signal to the treatment machine to inform the treatment machine that the imager 200 is about to obtain image(s) of the patient. In response to such signal, the treatment machine holds off the delivery of the treatment beam for a short amount of time—i.e., enough to allow the imager 200 to take the image(s) of the patient. After the desired image(s) has been obtained by the imager 200, the imager 200 (or its control, such as control 40 in FIG. 1) then sends another signal to the treatment machine to cause the treatment machine to resume its delivery of treatment beam.

In further embodiments, software processing may be employed to remove the artifact from the image. For example, an artifact-correction module may be utilized to process the image from the imager 200 in order to remove the artifacts in the image. In some embodiments, such artifact-correction module may be configured to detect the rectilinear (e.g., horizontal) bands and/or dark or bright lines in an image, and to remove such rectilinear bands and/or dark or bright lines. By means of non-limiting examples, the removal of the bands and lines in the image may be performed using a dedicated band and line suppression algorithm that corrects for the offset and gain errors, image smoothing function, pixel replacement, etc., or any combination of the foregoing.

In some embodiments, if a synchronization technique is employed, the resulting image may not include any artifacts. In other embodiments, employment of the synchronization technique may reduce some artifacts, but may not completely eliminate all of the artifacts. In such cases, the artifact-correction module may be employed to remove the few remaining artifacts that are present in the image.

It should be noted that the imager 200 described herein is not limited to withstand radiation resulted from treatment beam generated by electrons striking a target. In other embodiments, the imager 200 described herein may be for withstanding radiation resulted from other types of particle beams, such as proton beams. For example, the imager 200 described herein may be used with a proton treatment machine. In such cases, the features described herein may allow the imager 200 to withstand radiation resulted from the delivery of a proton treatment beam.

In addition, although the imager 200 described herein has been described with reference to medical applications, in other embodiments, the imager 200 described herein may be used in other applications, such as security inspection, material inspection, material discrimination, or in any other application which involves use of a linear accelerator or a radioactive source.

Furthermore, the imager 200 is not limited to having the scintillator layer 202. In other embodiments, the imager 200 may be other types of imager, such as those that may not require any scintillator layer. For example, as discussed, in other embodiments, the imager 200 may include a conversion layer that is configured to generate electron-hole pairs in response to radiation. In such cases, image signals are generated directly by the conversion layer, and the imager 200 may not include any scintillator layer. Also as similarly discussed, in further embodiments, the imager 200 may include photon counters configured to generate image(s) based on photon counting.

Specialized Processing System

Figure 7:
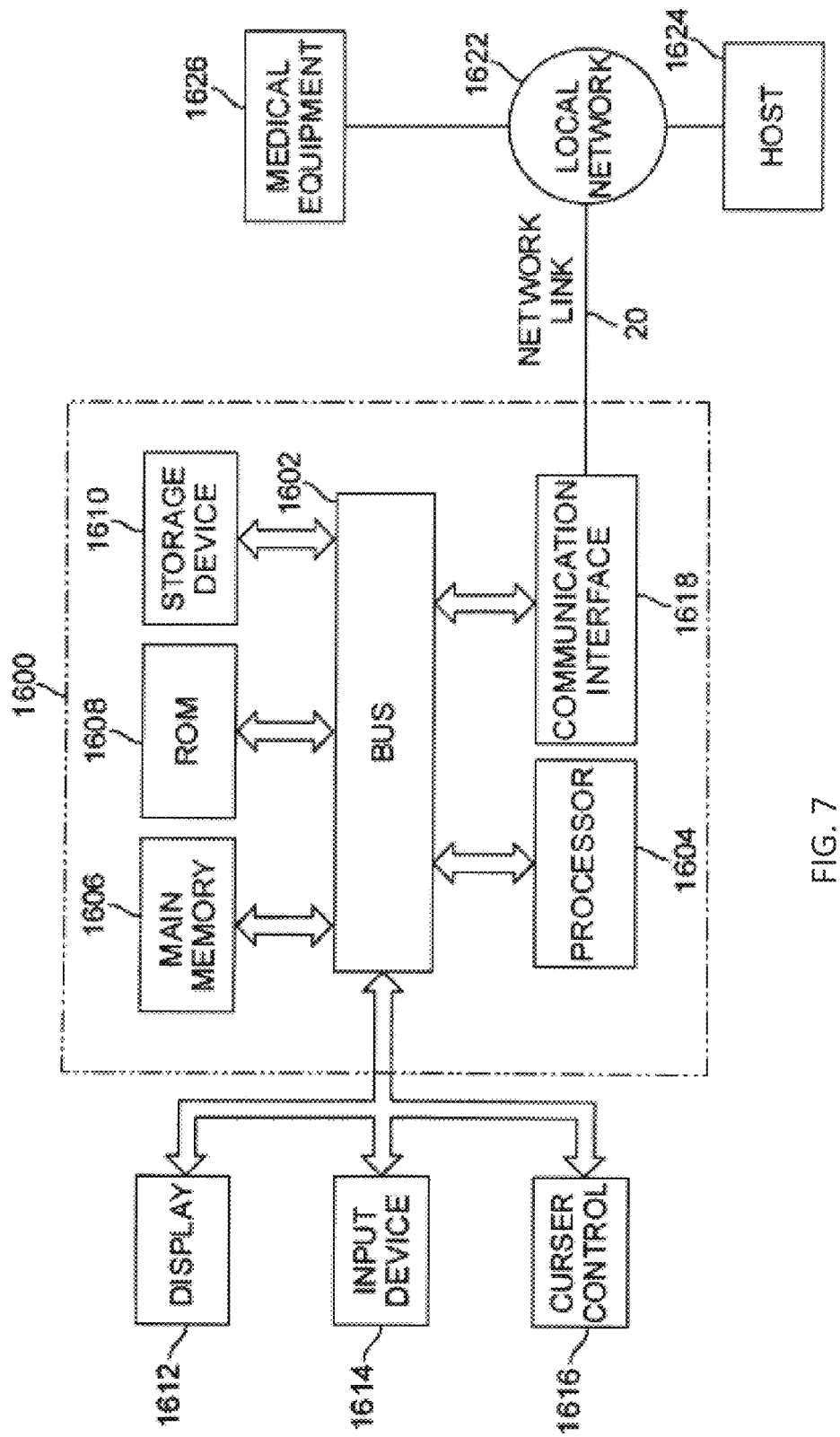
FIG. 7 illustrates a specialized processing system in accordance with some embodiments.

FIG. 7 is a block diagram illustrating an embodiment of a specialized processing system 1600 that can be used to implement various features described herein. For example, in some embodiments, the processing system 1600 may be used to implement the processing unit 54 of FIG. 1. The processing system 1600 may also be used to implement a control that controls an operation of the imager 200, and/or a control that controls an operation of the treatment machine. In further embodiments, the processing system 1600 may be used to implement the artifact-correction module.

Processing system 1600 includes a bus 1602 or other communication mechanism for communicating information, and a processor 1604 coupled with the bus 1602 for processing information. The processor system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The processor system 1600 further includes a read only memory (ROM) 1608 or other static storage device coupled to the bus 1602 for storing static information and instructions for the processor 1604. A data storage device 1610, such as a magnetic disk, solid state disk, or optical disk, is provided and coupled to the bus 1602 for storing information and instructions.

The processor system 1600 may be coupled via the bus 1602 to a display 167, such as a flat screen monitor, for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the processor system 1600 can be used to perform various functions described herein. According to some embodiments, such use is provided by processor system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another processor-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "processor-readable medium" as used herein refers to any medium that participates in providing instructions to the processor 1604 for execution. Such a medium may take many forms, including but not limited to, non-volatile media, volatile media, and transmission media. Non-volatile media includes, for example, optical, solid state or magnetic disks, such as the storage device 1610. A non-volatile medium may be considered an example of non-transitory medium. Volatile media includes dynamic memory, such as the main memory 1606. A volatile medium may be considered an example of non-transitory medium. Transmission media includes coaxial cables, copper wire and fiber optics, including the wires that comprise the bus 1602. Transmission media can also take the form of acoustic or light waves, such as those generated during radio wave and infrared data communications.

Common forms of processor-readable media include, for example, a flexible disk, hard disk, magnetic tape, or any other magnetic medium, a CD-ROM, any other optical medium, any other physical medium with patterns of holes, a RAM, a PROM, and EPROM, a FLASH-EPROM, solid state disks any other memory chip or cartridge, a carrier wave as described hereinafter, or any other medium from which a processor can read.

Various forms of processor-readable media may be involved in carrying one or more sequences of one or more instructions to the processor 1604 for execution. For example, the instructions may initially be carried on a magnetic disk or solid state disk of a remote computer. The remote computer can load the instructions into its dynamic memory and send the instructions over a network, such as the Internet. The processing system 1600 can receive the data on a network line. The bus 1602 carries the data to the main memory 1606, from which the processor 1604 retrieves and executes the instructions. The instructions received by the main memory 1606 may optionally be stored on the storage device 1610 either before or after execution by the processor 1604.

The processing system 1600 also includes a communication interface 1618 coupled to the bus 1602. The communication interface 1618 provides a two-way data communication coupling to a network link 1620 that is connected to a local network 1622. For example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source and/or an imaging device or a switch operatively coupled to a radiation beam source and/or an imaging device. The data streams transported over the network link 1620 can comprise electrical, electromagnetic or optical signals. The signals through the various networks and the signals on the network link 1620 and through the communication interface 1618, which carry data to and from the processing system 1600, are exemplary forms of carrier waves transporting the information. The processing system 1600 can send messages and receive data, including program code, through the network(s), the network link 1620, and the communication interface 1618.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. An imager comprising:
    an array of imager elements configured to generate image signals based on radiation received by the imager; and
    a circuit configured to perform readout of the image signals, wherein the circuit is configured to be radiation hard;
    wherein the imager is configured to remain fully functional even after the imager has been exposed to radiation resulting from at least 10 MV radiation beam with parameters of 100 kRad and 600 Mu/min.

2. The imager of claim 1, wherein the circuit is configured to withstand at least 100 kRad of radiation.

3. The imager of claim 1, wherein the circuit is configured to withstand at least 500 kRad of radiation.

4. The imager of claim 1, wherein the circuit comprises readout and control circuit coupled to the array of imager elements, wherein the readout and control circuit is radiation hard.

5. The imager of claim 1, wherein the circuit comprises a gate driver, and wherein the gate driver is radiation hard.

6. The imager of claim 1, wherein the circuit of the imager comprises a commercial component that is not marketed as radiation hard, but has been tested as meeting certain radiation hardness requirement.

7. The imager of claim 1, wherein the circuit of the imager comprise a commercial component that is marketed as radiation hard.

8. The imager of claim 1, wherein the circuit of the imager has a component that is custom-designed to meet certain radiation hardness requirement.

9. The imager of claim 1, further comprising a radiation shielding for protecting the imager from treatment radiation.

10. An imager comprising:
an array of imager elements configured to generate image signals for an image frame based on radiation received by the imager; and
a circuit configured to perform readout of the image signals, wherein the circuit is configured to be radiation hard;
wherein the circuit comprises a readout and control circuit coupled to the array of imager elements, wherein the readout and control circuit is configured to perform signal readout in synchronization with an operation of a treatment beam source;
wherein the readout and control circuit is configured to:
readout a first subset of the image signals for the image frame,
after the first subset of the image signals is readout, stop reading out any of the image signals to allow the treatment beam source to provide a treatment beam pulse, and
readout a second subset of the image signals for the image frame after the treatment beam source has provided the treatment beam pulse, the second subset of the image signals being different from the first subset of the image signals, and
wherein the first subset of the image signals and the second subset of the image signals are for different respective regions of the image frame.

11. The imager of claim 10, wherein the readout and control circuit is configured to start the signal readout for the image frame at a pre-determined time or within a predetermined time period with respect to the treatment beam pulse.

12. The imager of claim 10, wherein the treatment beam source is configured to hold off a delivery of the treatment beam pulse or multiple treatment beam pulses for a beam hold period.

13. The imager of claim 12, wherein the beam hold period is long enough to allow the imager to reset the array of imager elements, receive imaging dose, and readout some of the image signals.

14. The imager of claim 1, wherein the circuit comprises a layout configured to provide radiation hardness.

15. The imager of claim 14, wherein the circuit comprises an edge-less transistor, an enclosed layout transistor (EL T), at least two transistors with guard rings between the two transistors, or any combination of the foregoing.

16. An imager comprising:
an array of imager elements configured to generate image signals based on radiation received by the imager; and
a circuit configured to perform readout of the image signals, wherein the circuit is configured to be radiation hard;
wherein the array of imager elements is configured to generate image signals based on photon counting; and
wherein the circuit is configured to readout a first subset of the image signals before a delivery of a treatment radiation beam, and to readout a second subset of the image signals after the delivery of the treatment radiation beam, and wherein the first subset of the image signals and the second subset of the image signals are for different respective regions of an image frame.

17. An imager comprising:
an array of imager elements configured to generate image signals for an image frame based on the radiation received by the imager; and
a circuit coupled to the array of imager elements, wherein the circuit is configured to perform signal readout in synchronization with an operation of a treatment beam source; wherein
the circuit is configured to:
readout a first subset of the image signals for the image frame,
after the first subset of the image signals is readout, stop reading out any of the image signals to allow the treatment beam source to provide a treatment beam pulse, and
readout a second subset of the image signals for the image frame after the treatment beam source has provided the treatment beam pulse, the second subset of the image signals being different from the first subset of the image signals, and
the first subset of the image signals and the second subset of the image signals are for different respective regions of the image frame.

18. The imager of claim 17, wherein the circuit is configured to start the signal readout for the image frame at a pre-determined time or within a predetermined time period with respect to the treatment beam pulse.

19. The imager of claim 17, wherein the treatment beam source is configured to hold off a delivery of the treatment beam pulse for a beam hold period.

20. The imager of claim 19, wherein the beam hold period is long enough to allow the imager to reset the array of imager elements, receive imaging dose, and readout some of the image signals.

21. The imager of claim 17, wherein the circuit is configured to be radiation hard.

22. The imager of claim 17, wherein the circuit comprises readout and control circuit coupled to the array of imager elements, wherein the readout and control circuit is radiation hard.

23. The imager of claim 17, wherein the circuit comprises a gate driver, and wherein the gate driver is radiation hard.

24. The imager of claim 17, wherein the array of imager elements is configured to generate the image signals based on light signals provided by a scintillator layer.

25. The imager of claim 17, wherein the array of imager elements is configured to generate the image signals based on charges provided by a conversion layer.

26. The imager of claim 17, wherein the array of imager elements is configured to generate the image signals based on photon counting.

27. The imager of claim 17, wherein the circuit is configured to perform signal readout in synchronization with the operation of the treatment beam source to prevent a band artifact, a dark line artifact, a bright line artifact, or any combination of the foregoing.

28. The imager of claim 1, wherein the readout and control circuit is configured to suspend a signal-readout process when a treatment beam source is delivering a treatment beam pulse or multiple treatment beam pulses.

29. The imager of claim 1, wherein the readout and control circuit is configured to perform signal readout for one or more lines of the imager during a treatment session when a treatment beam source is not delivering treatment energy, and to suspend signal readout for another line of the imager when the treatment beam source is delivering treatment energy.

30. The imager of claim 1, wherein the array of imager elements is configured to generate the image signals based on light signals provided by a scintillator layer.

31. The imager of claim 1, wherein the array of imager elements is configured to generate the image signals based on charges provided by a conversion layer.

* * * * *